United States Patent [19]

Stepanov et al.

[11] 4,264,738

[45] Apr. 28, 1981

[54] PROCESS FOR PURIFICATION OF PROTEOLYTIC ENZYMES

[76] Inventors: Valentin M. Stepanov, ulitsa Chertanovskaya, 35, kv. 247; Galina N. Rudenskaya, ulitsa Tsandera 7, kv. 251, both of Moscow; Valery K. Akparov, ulitsa Lugovaya, 33, kv. 26, Fryazino, Moskovskoi oblasti; Anatoly V. Gaida, 3Dorozhny proezd, 5 korpus 2, kv. 45, Moscow, all of U.S.S.R.

[21] Appl. No.: 62,683

[22] Filed: Aug. 1, 1979

[51] Int. Cl.$^3$ .......................... C12N 9/56; C12N 9/64
[52] U.S. Cl. ...................... 435/222; 435/212; 435/213; 435/219; 435/223; 435/226; 435/815
[58] Field of Search ................ 435/176, 212, 219–226, 435/815

[56] References Cited

U.S. PATENT DOCUMENTS 4,100,028  7/1978  Stepanov et al. ................ 435/815 X

FOREIGN PATENT DOCUMENTS 551339  6/1977  U.S.S.R. .................................... 435/212

*Primary Examiner*—Lionel M. Shapiro
*Attorney, Agent, or Firm*—Burgess, Ryan and Wayne

[57] ABSTRACT

A process for purification of proteolytic enzymes which comprises a biospecific sorption on a sorbent comprising a product of interaction of a solid carrier which is an aminoderivative of a siliceous material, a ligand and a condensation agent; elution of the sorbed enzymes by salt buffers and/or organic solvents.

10 Claims, No Drawings

4,264,738

PROCESS FOR PURIFICATION OF PROTEOLYTIC ENZYMES

FIELD OF THE INVENTION

The present invention relates to the microbiological industry and, more particularly, to a process for purification of proteolytic enzymes.

Proteolytic enzymes are useful in medicine, biochemistry and food indsutry, as well as in the manufacture of detergents.

BACKGROUND OF THE INVENTION

The method of ion-exchange chromatography, in particular chromatography on modified silochromes (cf. USSR Inventor's Certificate No. 551339), is currently employed for the preparation of high-purity proteinases. This method however, is insufficiently selective, i.e. it does not enable the recovery of enzymes, in a high yield, directly from mixtures with a low concentration of the active enzyme containing a high amount of inorganic and organic impurities (e.g. from culture liquid).

For this reason, for the selective purification of enzymes the method of affine chromatography is more frequently employed. The method is based on the affinity of enzymes towards specific analogues of a substrate or inhibitors covalently bonded with the insoluble carrier thus making it possible to separate enzymes on the basis of their biological specificity and, consequently, obtain a higher degree of purification in comparison with other types of chromatographic techniques.

Known in the art are methods for purification of proteolytic enzymes comprising biospecific sorption on sorbents which are insoluble carriers, such as derivative of argarose, activated by means of a condensation agent, such as bromocyanogen, and covalently bonded with ligands. These substances are specific for a given class of enzymes such as gramicidin S, bacitracin, bacilliquine, phenylboric acid.

Sorption of enzymes on these sorbents is effected at a pH within the range of from 1.8 to 8.0 in salt buffers. Upon elution, an organic solvent is added to the salt buffer to ensure a complete desorption. The yield of enzymes in terms of activity is as high as 86%, the degree of purification is varied within the range of 2 to 95 times as compared to the starting material depending on its purity. However, sorbents produced, e.g. from sepharose which is a derivative of agarose contain 0.6 to 10 mcmol of the ligand per ml of a wet sorbent. This concentration of the ligand does not make it possible to ensure a maximum sorption of the enzyme per unit volume of the column, thus lowering the yield of the active enzyme per unit volume, which, in turn, lowers the process efficiency.

Furthermore, the above-mentioned sorbents have insufficient hydrodynamic properties. Thus, a solution of an enzyme is eluted from a column with 25 ml of phenylcarbonate sepharose at the rate of 10 ml/hr.

From a column with 28 of bacitracin-sepharose containing 10 μmol of the ligand per ml of a wet sorbent, there are obtained, directly from 500 ml of a culture liquid of Actinomyces Sp., 10 mg per hour of enzyme purified by 104 times as compared to the starting material.

The sorbents based on agarose cannot be employed in purification of solutions of proteinases containing enzymes destroying agarose as impurities.

The use of a highly-toxic bromocyanogen for activation of agarose or derivatives thereof hinders the preparation of large amounts of sorbents, thus increasing production costs thereof.

It is an object of the present invention to provide a process for purification of proteolytic enzymes which features a higher productivity due to increased output with high yield of enzymes of high purity and activity per unit volume and per unit time.

BRIEF SUMMARY OF THE INVENTION

This object is accomplished by a process for purification of proteolytic enzymes by biospecific sorption on a sorbent comprising a product of the reaction of a solid carrier, a ligand and a condensation agent, followed by elution of the sorbed enzymes by salt buffers and/or organic solvents, wherein, in accordance with the present invention, the sorbent is made of a product of the reaction of a solid carrier (which is an amino derivative of a siliceous material), said ligand and condensation agent.

The sorbents employed in the process according to the present invention have a high mechanical and heat strength, a macroporous structure, which makes it possible to improve their capacity, and hydrodynamic properties, as well as stability in storage.

Sorbents based on said aminoderivative of a siliceous material are not subjected to deterioration by microorganisms and agarose-destroying enzymes. As a result, the process efficiency is increased due to a higher yield of enzymes having an improved purity and increased activity per unit volume and unit time.

For the purpose of a further increase of the process efficiency, it is also preferred to use the product of interaction of aminosilochrome, benzoquinone, gramicidin S; the product of interaction of aminosilochrome, benzoquinone and bacitracin; the product of interaction of aminosilochrome, benzoquinone and bacilliquine, or the product of interaction of aminosilochrome, a water-soluble carbodiimide and n(ω-amino methyl) phenylboric acid; the product of interaction of aminosilochrome, hexamethylenediisocyanate and n(ω-aminomethyl)-phenylboric acid.

In the purification of carboxy proteinases, it is preferred to use, as a sorbent, a product of interaction of aminosilochrome, benzoquinone and gramicidin S, or bacilliquine, or bacitracin; the sorption should be conducted at a pH value ranging from 1.8 to 5.0.

In the purification of serine proteinases it is preferred to use, as the sorbent, a product of interaction of aminosilochrome, benzoquinone and bacitracin or bacilliquine; the sorption process should be effected in this case at a pH value ranging from 6.0 to 8.5.

In the purification of serine proteinases, as sorbents it is also preferred to use a product of interaction of aminosilochrome, n(ω-aminomethyl)phenylboric acid and a water-soluble carbodiimide or hexamethylenediisocyanate and the sorption should be conducted at a pH value ranging from 6.0 to 9.5 in the presence of glycerol; elution should be effected by means of a salt buffer with the addition of pentaerythritol.

The sorbents according to the present invention contain 6 to 100 mcmol of the ligand per 1 ml of a wet sorbent. Sepharase based sorbents contain 0.6 to 8 mcmol of the ligand per 1 ml of a wet sorbent. The increase in the amount of ligand per unit volume provides an increase in the capacity of a column containing the sorbent by about 25 times and, therefore, an increased output of the pure product from the column.

Furthermore, the sorbents of the present invention have better hydrodynamic properties. A solution of an enzyme is eluted from a column containing 25 ml of phenylborate-sepharose at the rate of 10 ml/hr, whereas the rate of elution from a column of the same volume of phenylborate-silochrome is 100 ml/hr. Due to the increased capacity of the sorbent, and higher rate of washing and elution of enzymes, it is possible to substantially increase the column efficiency.

Replacement of expensive bromocyanogen, employed in the synthesis of bacitracin-sepharose, with benzoquinone and carbodiimides necessitating no special conditions for handling and storage makes the synthesis of the sorbents according to the present invention more simple and accessible.

The process according to the present invention makes it possible to purify different proteolytic enzymes with a yield of 75 to 100%. The activity is increased by 1.5 to 100 times, as compared to the starting material, depending on the purity of the starting material.

The process according to the present invention is especially effective in recovering enzymes directly from a culture liquid containing colored impurities. The sorbents according to the present invention ensure recovery of substantially pure enzymes. Due to the high selectivity of the sorbents of the present invention, a considerable effect is obtained in a single-stage purification process.

Furthermore, the biospecific sorbents according to the present invention may be employed with solutions within a wide range of pH values of from 1.8 to 9.0 thus enabling their use for recovery of proteolytic enzymes of different classes including carboxy, serine, thiol and metal proteinases and exopeptidases.

DETAILED DESCRIPTION OF THE INVENTION

The process according to the present invention is practically embodied in the following manner.

A solution of a crude enzyme is brought into contact with a biospecific sorbent.

For the synthesis of sorbents according to the present invention as the insoluble carrier use is made of an aminoderivative of a siliceous material such as silochrome, pretreated with γ-aminopropyltriethoxysilane.

The resulting aminosilochrome reacts with ligands (such as antibiotic polypeptpides: bacitracin, bacilliquine, gramicidin S); as the condensation agent use is made of benzoquinone or with a ligand such as phenylboric acid; the condensation agent is a water-soluble carbodiimide. The corresponding reactions proceed according to the following scheme:

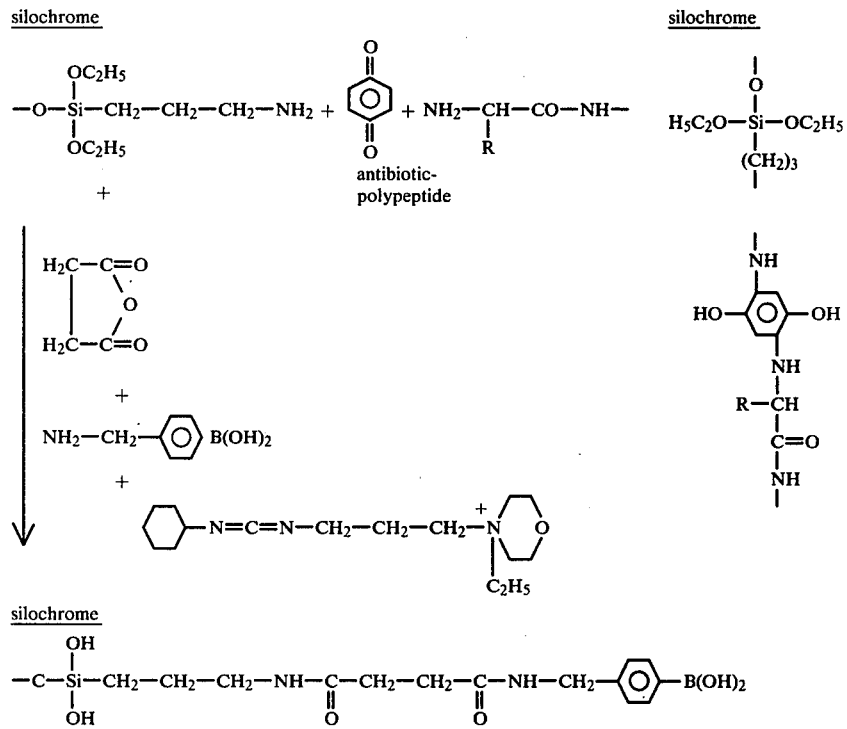

For a practical realization of the process according to the present invention there have been synthesized such specific sorbents as bacitracin-silochrome, baciliquine-silochrome, gramicidin-S-silochrome, phenylborate-silochrome.

The antibiotics-polypeptides employed as ligands are inhibitors of carboxy proteinases. This explains the specific interaction of the sorbent with proteolytic enzymes of various classes. The presence of aminoacids in molecules of the antibiotics and the structural arrangement characteristic of cyclopeptides hinder their splitting by enzymes.

Bacitracin comprises a naturally-occurring cyclododecapeptide containing three D-aminoacids. Bacilliquine is a crude preparation similar to bacitracin. In a molecule of another naturally-occurring cyclododecapeptidegramicdin S-hydrophobic aminoacids prevail. In constrast to bacitracin, which contains dicarboxylic aminoacids, gramicidin S contains a greater amount of neutral acids, as well as a diaminoacid, namely ornithine. Fine differences in the structure of molecules of the ligands enhance specificity of sorbents towards individual proteinases. In certain cases gramicidin-S-silochrome and bacitracinsilochrome are mutually complementing sorbents: the enzyme which is not absorbed on one of them may be successfully sorbed on the other. These properties of the sorbents may be employed for resolution of a mixture containing two proteolytic enzymes. Combined boric acids specifically react with serine proteinases with the formation of labile complexes with functional groups of an active center of the enzyme.

Phenylborate-silochrome possesses a group specificity in respect to the class of serine proteinases.

Sorption of enzymes on the sorbents according to the present invention is conducted under dynamic or static conditions. In carrying out the process of the present invention, proteinases are selectively combined with the insoluble carrier. The sorbent with the combined protein is then eluted with a corresponding buffer solution. This results in separation of impurities including coloured ones.

As the eluents, use is made of solution of salts having different concentrations. In the case where the enzyme is combined with the sorbent so strongly that it is impossible to elute it by means of salt solutions, organic solvents are mixed with the salt solution facilitating a more efficient desorption.

The purified enzyme is used in the form of a solution or lyophilically dried after desalting by gel-filtration or dialysis.

For a better understanding of the present invention some specific Examples are given by way of illustration.

In these Examples, illustrating purification of certain proteinases in a column with biospecific sorbents, the amount of the deposited and eluted protein is given in mg and in optical units, i.e. units of optical density at 280 nm.

Activity of enzymes is measured by the rate of hydrolysis of hemoglobin (Examples 1, 2 and 10); by the rate of milk coagulation (Examples 3 to 6); by the rate of splitting of synthetic substrates: α-carboxypropionyl-phenylalanine (Example 7) and -p-nitroanilide of car-bobenzoxy-L-alanyl-L-analyl-L-leucine (Examples 8, 11, 12, 13, 14, 15).

EXAMPLE 1

Purification of commercial preparation—pig pepsin on bacitracin-silochrome

For the synthesis of bacitracin-silochrome use is made of 1 g of aminosilochrome (340 mcmol of amino-groups per 1 g) in 0.1 M of NaHCO$_3$, pH 10.0; 34 mg of p-benzoquinone in 2 ml of absolute dimethylformamide and 220 mg of bacitracin. The mixture is carefully stirred for 4 hours and left overnight at the temperature of 5° C. Then the sorbent is thoroughly eluted with 0.1 M NaHCO$_3$, (pH=10), water, alcohol and, prior to the test, by all eluting solutions. The resulting dark-colored sorbent contains, according to the data obtained by the aminoacid analysis, 46 μmol of bacitracin per 1 g of the dry sorbent. To purify pepsin, a 0.1 M acetate buffer solution with the pH of 5.0 containing a non-purified proteinase with the specific activity of 23 a.u./o.u. is passed through a chromatographic column (5×0.5 cm) packed with bacitracin-silochrome. Then the sorbent is eluted with the starting buffer. The active enzyme is eluted with a 25% isopropylalcohol in a 1 M NaCl with the pH of 5.0. The specific activity of the pig pepsin in the eluate is 34 a.u./mg. The yield in terms of activity is 100%, the purification is 1.5 times as compared to the starting material.

EXAMPLE 2

Purification of commercial preparation—pig pepsin on bacilliquine-silochrome

The commercial preparation of bacilliquine contains an insoluble filler. To recover bacilliquine, the preparation is thrice extracted with boiling methanol or ethanol. The extracts are evaporated in vacuum to a small volume. The residue of bacilliquine precipitated upon cooling is filtered-off and dried.

For the synthesis of bacilliquine-silochrome use is made of 100 g of aminosilochrome (120 mcmol of amino groups per 1 g) in a 0.1 M NaHCO$_3$ (pH=10), 864 mg of p-benzoquinone in 50 ml of absolute dimethylformamide and 12.8 g of bacilliquine. The mixture is carefully stirred for 4 hours and left overnight at the temperature of 5° C. Then the sorbent is carefully washed with a 0.1 M NaHCO$_3$ (pH=10), water, alcohol and, prior to the experiment, with all eluting solutions. The resulting dark-colored sorbent contains, according to the data of aminoacid analysis, 16 mcmol of bacilliquine per 1 g of the dry sorbent. To purify the pepsin, a 0.1 M acetate buffer solution (pH=5.0) containing the non-purified proteinase with the specific activity of 22 a.u./o.u. is passed through a chromatographic column packed with bacilliquine-silochrome (5×0.5 cm). Then the sorbent is eluted with the starting buffer. The active enzyme is eluted with a 25% isopropyl alcohol in a 1 M NaCl (pH=5.0). The specific activity of the pig pepsin in the eluate is 34 a.u./mg. The yield in terms of activity is 100%, purification is 1.5 times higher as compared to the starting material.

EXAMPLE 3

Purification of proteinase from Trichoderma lignorum on bacitracin-silochrome

The synthesis of bacitracin-silochrome is effected following the procedure described in the foregoing Example 1. A 0.1 M acetate buffer with the pH=5.0 containing 4 g of protein (a crude mixture of proteinases and cellulases) with the specific activity of 13.0 a.u./o.u. is passed through a chromatographic column (6×1.5 cm) filled with bacitracin-silochrome. Then the sorbent is washed with the starting buffer and successively eluted with a 1 M NaCl in the same buffer and 25% isopropanol in a 1 M NaCl (pH=5.0). The salt (I) and isopropanol (II) fractions of the eluate containing active protein are collected. Specific activity of fraction I is 216 a.u./o.u. Purification is 16.6 times as compared to the starting material. Specific activity of fraction II-58.6 a.u./o.u. Purification is by 4.4 times compared to the starting material. The yield of active protein is 97%.

EXAMPLE 4

Purification of ultrafiltrate of culture liquid of basidal fungus Russula decdoraus Fr-0456 on bacitracin-silochrome.

The synthesis of bacitracin-silochrome is conducted following the procedure described in the foregoing Example 1. The ultrafiltrate of the culture liquid with a pH of 4.5 and specific activity of 13 a.u./o.u. determined by coagulation of milk is passed through a chromatographic column (6×1.5 cm) filled with bacitracinsilochrome and balanced by means of a 0.1 M acetate buffer with the pH value of 4.5. Then the sorbent is washed with the starting buffer and successively eluted with a 1 M NaCl (pH=4.5) in the same buffer (fraction I) and 25% isopropanol in a 1 M NaCl (pH=5.0), (fraction II). The specific activity of fraction I is 664 a.u./o.u. purification is ensured by 51 times as compared with the starting material; the specific activity of fraction II is 260 a.u./o.u.; purification is obtained by 51 times higher as compared with the starting material. The yield of active protein is 100%.

EXAMPLE 5

Purification of ultrafiltrate of culture liquid of basidal fungus Russula decolorans Fr-0456 on bacilliquine-silochrome The synthesis of bacilliquine-silochrome is conducted following the procedure described in Example 2. The ultrafiltrate of the culture liquid (pH=4.5) with the specific activity of 3.3 a.u./o.u. is passed through a chromatographic column (5×0.5 cm) packed with bacilliquine-silochrome and balanced by means of a 0.1 M acetate buffer with the pH of 4.5. Then the sorbent is washed with the same buffer. The active enzyme is eluted with a 20% isopropanol in a 1 M NaCl, pH=4.5. The specific activity of the enzyme in the eluate is 120 a.u./o.u.; purification is by 36 times as compared with the starting material. The yield in terms of activity is 90%.

EXAMPLE 6

Isolation of two proteinases from a dry extract of a culture liquid of basidal fungus Russula decolorans Fr-0456 by means of bacilliquine-silochrome and gramicidin-S-silochrome The extract containing an enzyme with the specific activity of 180 a.u./o.u. is passed through a chromatographic column (25×1.5 cm) with bacilliquine-silochrome balanced with a 0.1 M acetate buffer with the pH=4.5. The solution passed through the sorbent is collected; the solution contains proteinase I. The specific activity of the solution is 2.6 a.u./o.u. The column is washed with the starting buffer. Proteinase II sorbed in the column is eluted with a 20% isopropanol in a 1 M NaCl with the pH=4.5. The specific activity of the enzyme in the eluate is 380 a.u./o.u. The yield in terms of activity is 80%; purification by 2.4 times as compared with the starting material.

The solution containing proteinase I non-sorbed on bacilliquine-silochrome is passed through a chromatographic column (18×1 cm) packed with gramicidin-S-silochrome.

To produce the sorbent use is made of 50 g of aminosilochrome (50 mcmol of amino groups per 1 g) in a 0.1 M NaHCO$_3$, pH=10; 162 mg of p-benzoquinone in 30 ml of dehydrated dimethylformamide and 1.2 g of gramicidin-S. The synthesis conditions are the same as in Examples 1 and 2.

The column with sorbed proteinase I is washed with a 0.1 M acetate buffer with the pH=4.5; the active enzyme is eluted with a 20% isopropanol in a 1 M NaCl, pH=4.5. The specific activity of the enzyme in the eluate is 370 a.u./o.u.; purification is by 3.7 times as compared with the starting material the yield in terms of activity is 60%.

EXAMPLE 7

Purification of α-chymotrypsin on phenyl-borate silochrome

For the synthesis of the sorbent use is made of aminosilochrome (415 mcmol of amino groups per 1 g), succinic anhydride and p-(ω-aminomethyl)-phenylboric acid chlorohydrate.

3 g of aminosilochrome are treated for 20 minutes at the temperature of 20° C. with a solution of 1 g of succinic anhydride in 9 ml of dimethylformamide. The excess of anhydride is removed by washing with 50 ml of dimethylformamide and water. To 3 g of the resulting succinylsilochrome there are added 333 mg of p-(ω-aminomethyl)phenylboric acid chlorohydrate in 15 ml of water. Then at the pH=5.0 there are added 3 g of a water-soluble carbodiimide. The mixture is maintained for 1 hour at the temperature of 20° C. under careful discontinuous stirring. The sorbent is filtered-off and washed with large amounts of water; prior to the experiment it is eluted with all eluting solutions. The resulting phenylborate-silochrome contains 215 mcmol of ligand per 1 g of the dry sorbent (or 100 mcmol per 1 ml of the dry sorbent). Fed into the column with 2 ml of phenylborate-silochrome is a solution of 10 m of α-chymotrypsin in 10 ml of a 0.05 M phosphate buffer with the pH=7.5. The specific activity of the solution is 0.025 a.u./mg. Then the sorbent is washed with 50 ml of the starting buffer, 1 M NaCl in the same buffer; 0.5 M glycerol in the same buffer, phosphate buffer with the pH=9 and the protein is eluted with 0.05 M pentaerythritol in 0.05 M phosphate buffer with the pH=9. There are obtained 5.9 mg of the protein with the specific activity of 0.053 a.u./mg. The yield in terms of activity is 100%; purification is by 2 times as compared with the starting material.

EXAMPLE 8

Purification of subtilysine A-50 on phenylborate-silochrome

Into a column with 4 ml of phenylborate-silochrome produced as in the foregoing Example 7 and balanced with a 0.05 M phosphate buffer with the pH=7.5 there are introduced 40 ml of a culture liquid of Bac.subtilis A-50 with the pH=7.5 and specific activity of 0.08 a.u./mg in hydrolysis of Z-L-Ala-L-Ala-L-Len-pNA. The column is successively washed with a 0.05 M phosphate buffer, (pH=7.5), 1 M NaCl in the same buffer, 0.5 M glycerol in the same buffer and a 0.05 M phosphate buffer with the pH=9. The active protein is eluted with a 0.5 M pentaerythritol in a 0.05 M phosphate buffer with the pH=9. After desalting and lyophilization there are obtained 2.26 mg of the protein with the specific activity of 1.08 a.u./mg; the yield is 80%, purification by 13.7 times as compared with the starting material.

EXAMPLE 9

Synthesis of phenylborate-silochrome using hexamethylenedisocyanate as the condensation agent To 1 g of aminosilochrome (340 mcmol of NH$_2$-groups) there is poured an excess of hexamethylenedisocyanate and allowed to stay for 15 minutes at room temperature, then washed with dimethylformamide and water to give a sorbent containing 30 mcmol of isocyanate groups per 1 g of the carrier. To 1 g of this sorbent poured is a solution of 200 mg of p-(ω-aminomethyl-)-phenylboric acid in 5 ml of dimethylformamide and left for 20 minutes at room temperature, whereafter the excessive amount of the reagents is washed-off with dimethyl-formamide and water. There is obtained phenylborate-silochrome with the ligand content of 150 mcmol/g.

EXAMPLE 10

Purification of pepsin on gramicidin-S-silochrome

To a solution of 25 mg of the preparation of pig pepsin in 10 ml of a 0.05 M versatile buffer with the pH=1.8 there are added 200 mg of gramicidin-S-silochrome, stirred for 20 minutes, the solution is decanted, the sorbent is washed for 5 times with portions of 5 ml each of the versatile buffer (pH=1.8) and pepsin is twice eluted with 5 ml of a 0.1 M NaCl in a 0.05 M versatile buffer (pH=1.8) containing 25% of isopropanol. The yield in terms of activity is 30%; purification is by 10 times as compared to the starting material.

EXAMPLE 11

Purification of subtilisine BPN' on bacitracin-silochrome

To a solution of 25 mg of subtilisine BPN' ("Serva") in 10 ml of a versatile buffer (ph=6.0) there are added 200 mg of bacitracin-silochrome, stirred for 20 minutes, the sorbent is washed with portions of 5 ml of a 0.05 M versatile buffer (pH=6.0) for 5 times and subtilisine is eluted twice with portions of 5 ml of a 0.1 M NaCl in a 0.05 M versatile buffer (pH=6.0) containing 25% of isopropanol. Subtilisine BPN is obtained with the yield of 45%; it has the activity relative to Z-L-Ala-L-Ala-L-Leu-pNA of 1.5 a.u./mg; purification of 1.5 times as compared to the starting material.

EXAMPLE 12

Purification of subtilisine 72 on bacitracin-silochrome

Into a column with 10 ml of bacitracin-silochrome balanced with 50 mM of tris-buffer (pH=8.5) there is added a solution of 2 g of a commercial preparation of subtilisine 72 (Protosubtilin GZh) with the specific activity of 0.166 a.u./mg. The column is washed with 50 mM tris-buffer (pH=8.5), then with a 1 M NaCl in the same buffer. The active enzyme is eluted with a 1 M sodium chloride in a 50 mM tris-buffer (pH=8.5) containing 20% of isopropanol. As a result, there are obtained 56 mg of the preparation with the specific activity of 7.7 a.u./mg. The yield in terms of activity is 130%; purification is by 46 times as compared with the starting material.

EXAMPLE 13

Purification of alkaline serine proteinase Bac. licheniformis on phenylborate-silochrome Into a column with 4 ml of phenylborate-silochrome (200 mcmol of the ligand per 1 g of the sorbent) balanced with 0.5 M glycerol in a 0.05 M phosphate buffer (pH=6.0) a solution of 10 mg of a commercial preparation of serin protease Bac.licheniformis in 5 ml of the same buffer is introduced. The column is washed with the same buffer, 1 M NaCl in 0.05 M phosphate buffer (pH=6.0) and 0.05 M phsophate buffer (pH=9.5). The proteinase is eluted with a 0.5 M pentaerythritol in 0.05 M phosphate buffer (pH=9.5). The yield in terms of activity is 150%; purification is 5.6 times as compared to the starting material. The resulting preparation has the specific activity determined by hydrolysis of Z-L-Ala-L-Ala-L-Leu-pNA of 18 a.u./mg.

EXAMPLE 14 (comparative)

Purification of culture liquid Actinomyces Sp. on columns with the same volume of bacitracin-sepharose and bacilliquine silochrome Into columns with bacilliquine-silochrome (28 ml) and bacitracin-sepharose (28 ml) there are introduced 500 ml (into each column) of a culture liquid of Actinomyces Sp. with the specific activity relative to the synthetic substrate A-L-Ala-L-Ala-L-Leu-pNA of 0.09 mcmol/min/o.u.

| Sorbent | Ligand amount in ml | Introduced activity, units | Obtained activity, units | Yield, activity, % | Spec. activity | Purification, times | Weight, mg | Time, hours |
|---|---|---|---|---|---|---|---|---|
| Bacitracin-sepharose | 10 mcmol | 1,800 | 2,128ˣ | 118 | 9.3 | 104 | 120 | 12 |
| Bacilliquine-silochrome | 32 mcmol | 1,800 | 3,080ˣ | 171 | 12.4 | 138 | 150 | 6 |

ˣinhibitors of proteinases are contained in the culture liquid. During the process of purification therefrom the total activity is increased.

The yield is 25 mg/hr with the use of bacilliquine-silochrome and 10 mg/hr with the use of bacitracinsepharose (prototype).

EXAMPLE 15 (comparative)

Purification of culture liquid of Bac.subtilis A-50 on columns with the same volume of phenylborate-sepharose and phenylborate-silochrome Into a column with phenylborate-sepharose (25 ml) there is added 1 ml of a culture liquid of Bac.subtilis with the specific activity of 0.043 a.u./ml (the column volume does not make it possible to introduce more), whereas into the column with phenylborate-silochrome (25 ml) there is introduced a culture liquid of Bac.subtilis 500 ml with the specific activity of 0.08 a.u./ml according to Z-L-Ala-L-Ala-L-Leu-pNA

| Sorbent | Ligand amount in ml | Introduced a.u. | Obtained a.u. | Yield on activity, % | Specific activity | Purification, times | Weight, mg | Time, hours |
|---|---|---|---|---|---|---|---|---|
| Phenylborate-sepharose | 5 μmol | 2.2 | 2.2 | 100 | 1.8 | 44 | 1.5 | 2 |

-continued

| Sorbent | Ligand amount in ml | Introduced a.u. | Obtained a.u. | Yield on activity, % | Specific activity | Purification, times | Weight, mg | Time, hours |
|---|---|---|---|---|---|---|---|---|
| Phenylborate-silochrome | 100 μmol | 200 | 160 | 80 | 1.1 | 13.7 | 160 | 4 |

The yield is 40 mg of the enzyme per hour with the use of phenylborate-silochrome and 0.75 mg/hr with the use of penhylborate-sepharose.

What is claimed is:

1. A process for purification of proteolytic enzymes comprising a biospecific sorption of dissolved proteolytic enzymes on a sorbent prepared by interaction of an aminoderivative of a siliceous material, a condensation agent and a ligand; elution of the sorbed proteolytic enzymes with salt buffers, organic solvents or mixtures thereof.

2. A process according to claim 1, wherein use is made of a product of interaction of aminosilochrome, benzoquinone, gramicidin-S.

3. A process according to claim 1, wherein use is made of a product of interaction of aminosilochrome, benzoquinone and bacitracin.

4. A process according to claim 1, wherein use is made of a product of interaction of aminosilochrome, benzoquinone and bacilliquine.

5. A process according to claim 1, wherein use is made of a product of interaction of aminosilochrome, a water-soluble carbodiimide and p-(ω-aminomethyl)-phenylboric acid.

6. A process according to claim 1, wherein use is made of a product of interaction of aminosilochrome, hexamethylenediisocyanate and p-(ω-aminomethyl)-phenylboric acid.

7. A process according to claim 1, wherein in purification of carboxy proteinases as the sorbent use is made of a product of interaction of aminosilochrome, benzoquinone and a ligand selected from the group consisting of gramicidin-S, bacitracin and bacilliquine; sorption being conducted at pH of from 1.8 to 5.0.

8. A process according to claim 1, wherein in purification of serine proteinases as the sorbent use is made of a product of interaction of aminosilochrome, benzoquinone and a ligand selected from the group consisting of bacitracin and bacilliquine; the sorption being conducted at a pH of from 6.0 to 8.5.

9. A process according to claim 1, wherein in purification of serine proteinases as the sorbent use is made of a product of interaction of aminosilochrome, p-(ω-aminimethyl)-phenylboric acid and a condensation agent selected from the group consisting of carbodiimide and hexamethylenediisocyanate, the sorption being conducted at a pH of from 6.0 to 9.5.

10. A process according to claim 9, wherein said sorption of serine proteinases is conducted in the presence of glycerol and elution is effected by means of a salt buffer in the presence of pentaerythritol.

* * * * *